United States Patent [19]
Kamiya et al.

[11] Patent Number: 5,314,590
[45] Date of Patent: May 24, 1994

[54] METHOD FOR CLEANING AND DISINFECTING SOFT CONTACT LENS AND TREATING SOLUTION FOR SOFT CONTACT LENSES

[75] Inventors: Hideaki Kamiya, Gifu; Makoto Nakagawa, Aichi, both of Japan

[73] Assignee: Tomei Sangyo Kabushiki Kaisha, Aichi, Japan

[21] Appl. No.: 38,300

[22] Filed: Mar. 29, 1993

Related U.S. Application Data

[62] Division of Ser. No. 700,177, May 20, 1991, Pat. No. 5,246,552.

[30] Foreign Application Priority Data

| | | | |
|---|---|---|---|
| Sep. 21, 1989 | [JP] | Japan | 1-246798 |
| Apr. 28, 1990 | [JP] | Japan | 2-114463 |
| Jul. 4, 1990 | [JP] | Japan | 2-178043 |

[51] Int. Cl.⁵ .................................... C25B 1/00
[52] U.S. Cl. .................. 204/131; 204/DIG. 6; 204/130
[58] Field of Search ............ 204/131, 130, DIG. 6; 131/1, 42

[56] References Cited

U.S. PATENT DOCUMENTS

| | | | |
|---|---|---|---|
| 4,396,583 | 8/1983 | LeBoeuf | 422/301 |
| 4,485,027 | 11/1984 | Rossmann et al. | 252/90 |
| 4,521,375 | 6/1985 | Houlsby | 422/29 |
| 4,568,517 | 2/1986 | Kaspar et al. | 422/30 |
| 4,614,549 | 9/1986 | Ogunbiyi et al. | 134/19 |
| 4,732,185 | 3/1988 | Cowle et al. | 134/84 |
| 4,820,352 | 4/1989 | Riedhammer et al. | 134/30 |
| 4,836,859 | 6/1989 | Konishi et al. | 134/1 |
| 4,921,544 | 5/1990 | Cowle et al. | 134/1 |
| 5,129,999 | 7/1992 | Holland et al. | 204/131 |
| 5,135,623 | 8/1992 | Dziabo et al. | 204/101 |

FOREIGN PATENT DOCUMENTS

| | | |
|---|---|---|
| 3806953 | 9/1989 | Fed. Rep. of Germany . |
| 2451195 | 11/1980 | France . |
| 63-35023 | 3/1963 | Japan . |
| 56-68454 | 6/1981 | Japan . |
| 57-153653 | 9/1982 | Japan . |
| 60-7060 | 3/1985 | Japan . |
| 60-217333 | 10/1985 | Japan . |
| 63-193129 | 8/1988 | Japan . |
| WO89/00430 | 1/1989 | PCT Int'l Appl. . |

*Primary Examiner*—John Nielbing
*Assistant Examiner*—Arun S. Phasge
*Attorney, Agent, or Firm*—Armstrong, Westerman, Hattori, McLeland & Naughton

[57] ABSTRACT

An method for cleaning and disinfecting a soft contact lens, characterized by immersing the soft contact lens in a treating solution which does not generate any hypohalite during electrolysis, supplying a direct current, and raising the temperature of the treating solution; and a treating solution for a soft contact lens, characterized by containing a treating agent mainly composed of boric acid and borax in a concentration of at most 2.2 w/v % and having an electrical conductivity of at most 8 mS/cm are disclosed.

3 Claims, 3 Drawing Sheets

METHOD FOR CLEANING AND DISINFECTING SOFT CONTACT LENS AND TREATING SOLUTION FOR SOFT CONTACT LENSES

This is a division, of application Ser. No. 07/700,177, filed May 20, 1991 now U.S. Pat. No. 5,246,552.

TECHNICAL FIELD

The present invention relates a method for cleaning and disinfecting a soft contact lens and a treating solution for a soft contact lens.

BACKGROUND ART

A soft contact lens (hereinafter referred to as lens) has some apprehensions that eyes are injured when the lens is continuously worn in eyes as it is for a long period of time because stains in the surroundings, microbes, proteins contained in tear fluid, and the like adhere to the lens while the lens is worn in eyes. Accordingly, there is a necessity to clean or disinfect the lens regularly, preferably every day.

As a method for cleaning a lens, a method comprising washing a lens with a solution containing a surface active agent by fingers has been conventionally carried out, and according to the method, stains on the surface of the lens can be removed. However, stains such as proteins got into the internal of a lens cannot be removed. Further, when the lens is boiled to disinfect as it is, denaturation or coagulation of the proteins being got into a lens proceeds, and denatured proteins or coagulated proteins are more stiffly adhered to the lens. As a result, there occurs a problem of generation of cloudiness of the lens.

As a cleaning agent for reusing a lens stained with proteins, a cleaning agent containing a proteolytic enzyme has been conventionally known. However, according to the cleaning method of using this cleaning agent, although proteins adhered to the surface of a lens can be decomposed, besides taking a long period of time for revealing the cleaning effects, sufficient removing effects of proteins cannot be revealed because the proteolytic enzyme itself should be immersed into the internal of a lens so that proteins being denatured in the internal of a lens can be decomposed.

Also, U.S. Pat. No. 4,732,185 discloses a method for cleaning a lens comprising establishing an electric field in a determined direction in a boric acid-EDTA buffer solution having a range of pH 8 to 9 and immersing a lens in the solution to remove proteins from the lens by electrophoresis. When this method is carried out, contaminated proteins in the internal of the lens can be removed. However, the method requires that proteins should not be denatured nor ionized, and there are some problems in the method such that it takes a long period of time for the treatment. Further, according to the method disclosed in the above U.S. Patent, boric acid is used in a high concentration such as 0.808 mol/l and pH is kept at an alkaline level of 8 to 9 so that a lens can be disinfected by antiseptic effect and disinfecting effect of boric acid because the lens cannot be heated to prevent thermal denaturation of proteins. When boric acid is used in such a high concentration, disinfecting effect is exhibited. However, since pH and/or osmotic pressure are/is too high, wearing a lens in eyes after the treatment is dangerous, and there is a problem in safety for eyes.

On the other hand, as a method for disinfecting a lens, a method comprising immersing a lens in a sodium chloride aqueous solution and generating hypochlorite by applying an electric current to the solution to disinfect the lens, disclosed in Japanese Unexamined Patent Publication No. 68454/1981 and Japanese Unexamined Patent Publication No. 153658/1982, a method comprising immersing a lens in an $H_2O_2$ aqueous solution to disinfect the lens and decomposing $H_2O_2$ with a metallic catalyst, a reducing agent and an enzyme catalyst to make the solution harmless, disclosed in Japanese Unexamined Patent Publication No. 38559/1983, Japanese Unexamined Patent Publication No. 68858/1985 and Japanese Unexamined Patent Publication No. 217333/1985, and the like have been known other than the above-mentioned method for disinfecting a lens comprising boiling a lens to disinfect.

However, according to the method of generating hypochlorite by electrolysis, it takes a long period of time for the natural disappearance of hypochlorite remaining in a treating vessel after disinfecting, and the procedures are also complex because the solution should be reduced so that hypochlorite does not remain in a lens. Further, when the above procedures are applied to a colored contact lens or a dye-marked lens, there are some problems such that decoloration or discoloration of the colored lens or the dye-marked lens occurs due to the above treatment.

Also, according to the method of using an $H_2O_2$ aqueous solution, besides taking a long period of time for the treatment since $H_2O_2$ remaining in the lens should be decomposed, stimulation such as smarting of eyes occurs if $H_2O_2$ remaining in the internal of the lens is not completely decomposed. Therefore, the above method is not a suitable disinfecting method.

As a soaking solution for soft contact lenses, saline solution; liquid agents prepared by adding a preservative such as thimerosal, chlorhexidine, methylparaben, propylparaben or sorbic acid, and a chelating agent such as ethylene diaminetetraacetic acid, gluconic acid or citric acid to saline solution; liquid agents prepared by dissolving a tablet of the above-mentioned compounds in purified water or distilled water on use, and the like have been known.

However, when a soft contact lens is immersed in these soaking solutions for soft contact lenses and a direct current is applied to the solutions to clean and disinfect the soft contact lenses, chlorine ion existing in the solutions forms hypochlorite, and thereby there occurs some problems that the hypochlorite deteriorates the material of the soft contact lenses, and further colored soft contact lenses or dye-marked soft contact lenses are decolored or discolored.

It is an object of the present invention to provide a method of cleaning a lens giving no wrong influence to eyes, having safety for eyes and excellent detergency, and also disinfecting the lens.

Also, it is the second object of the present invention to provide a treating solution for soft contact lenses giving no wrong influence to eyes, having safety for eyes, and also giving no wrong influences to soft contact lenses when the soft contact lenses are electrically treated.

Further, it is the third object of the present invention to provide a treating solution for soft contact lenses having a property mechanically distinguishable from conventional treating solutions for soft contact lenses when the conventional treated solutions are misguidedly used.

DISCLOSURE OF INVENTION

The present invention relates to
(1) a method for cleaning and disinfecting a soft contact lens, characterized by immersing the lens in a treating solution which does not generate any hypohalite during electrolysis, supplying a direct current, and raising the temperature of the treating solution; and
(2) a treating solution for a soft contact lens, characterized by containing a treating agent mainly composed of boric acid and borax in a concentration of at most 2.2 w/v % and having an electrical conductivity of at most 8 mS/cm.

BEST MODE FOR CARRYING OUT THE INVENTION

Figure 1:
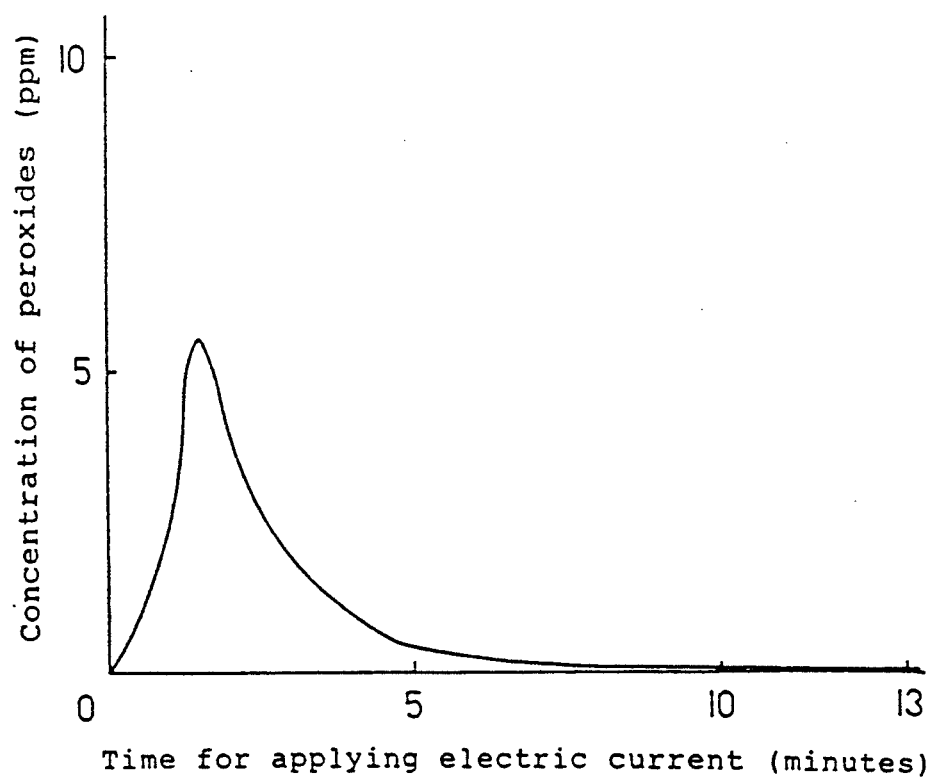
FIG. 1 is a graph showing the relation between the time for applying an electric current and the concentration of peroxides in the treating solution when voltage of 60 V and an initial electric current of 0.2 A are applied.

When charged particles exist in a treating solution in a colloidal state, and electrodes are inserted in the treating solution containing the particles, the particles move toward one of the electrodes by applying a direct current to form an electric field. This phenomenon is electrophoresis, and in the present invention, proteins are removed from the internal and surface of a lens by utilizing this nature of electrophoresis. Also, in the present invention, the generation of peroxides in the treating solution is utilized. The peroxides are generated when a direct current (hereinafter referred to as electric current) is applied to the treating solution which does not generate hypohalogenous acid salts under the condition the current value exceeds a certain value. The present invention relates to a method for boiling and disinfecting a lens by heating the treating solution with an aid of electrical resistance of the solution as well as cleaning a lens by decomposing proteins existed in a lens with an aid of generated peroxides and removing the decomposed proteins.

According to the present invention, since protein solubility can be imparted effectively by peroxides generated when an electric current is applied to the treating solution in which a lens is immersed, the removal of stains such as proteins can be finished in an extremely shortened period of time. The mechanism of decomposition of proteins has not yet been obvious, but it is supposed that the peroxides probably function in break of peptide bonds of proteins like hydrolysis.

In the present invention, since the peroxides are generated by an electrode reaction when an electric current is applied to the treating solution, there is no necessity to prepare a specific peroxides solution. Also, since the peroxides decrease when the treating solution is boiled by the heat due to electric resistance and the peroxides almost disappear after the treatment, the peroxides do not remain in a lens and there is no necessity of a troublesome operation such as reduction. Accordingly, after the treatment is carried out only by immersing a lens in the treating solution, the lens can be worn in eyes as it is.

In the present invention, as a treating solution, a treating solution not generating hypohalogenous acid salts but generating peroxides is used. As concrete examples of the treating solution, for instance, an aqueous solution containing a treating agent of which main components are boric acid and borax, buffer solutions such as Veronal buffer solution, Veronal-acetate buffer solution, tris-glycine buffer solution, tris-citric acid buffer solution, alanine-acetic acid buffer solution, glycine-acetic acid buffer solution, boric acid salt buffer solution, phosphoric acid salt buffer solution, citric acid salt buffer solution, acetic acid salt buffer solution, oxalic acid salt buffer solution, tris-EDTA buffer solution, succinic acid salt buffer solution and tartaric acid salt buffer solution; aqueous solutions such as $K_2CO_3$ aqueous solution, $Na_2CO_3$ aqueous solution, $NaHCO_3$ aqueous solution, $Na_2SO_4$ aqueous solution, $(NH_4)_2SO_4$ aqueous solution and $CH_3COONa$ aqueous solution are cited, and these treating solutions can be used alone or in admixture thereof. Among these, from the viewpoint of not affecting wrong influences to the material, standard and shape of a lens and safety for eyes even when the treating solution is accidentally got into eyes, treating solutions such as an aqueous solution containing a treating agent of which main components are boric acid and borax, phosphoric acid salt buffer solution, acetic acid salt buffer solution, citric acid salt buffer solution and boric acid salt buffer solution are particularly preferable.

Also, when an aqueous solution containing a treating agent of which main components are boric acid and borax is prepared so that the osmotic pressure of the aqueous solution is equal to that of a sodium chloride aqueous solution, the electric conductivity of the solution is lower than that of the sodium chloride aqueous solution. Accordingly, when the voltage applied to the aqueous solution is equal to the voltage applied to the sodium chloride aqueous solution, the current value in the sodium chloride aqueous solution is higher than that in the above aqueous solution. For instance, the electric conductivity of saline solution is 14.5 mS/cm, and the electric conductivity of generally used soaking solutions for soft contact lenses is 10 to 15 mS/cm. To the contrary, the electric conductivity of the aqueous solution containing a treating agent of which main components are boric acid and borax is at most 8 mS/cm as mentioned later.

Accordingly, even when conventional treating solutions for contact lenses of which main component is sodium chloride is misguidedly used instead of the treating solution according to the present invention, misuse of the treating solution can be previously prevented by using an apparatus for treating soft contact lenses with a means for detecting the change of an electric current value and stopping the electric current when an over-electric current is applied to the solution, such as fuse or breaker. These fuse and breaker have some advantages that they do not necessitate a complex circuit and that they are inexpensive.

The aqueous solution containing a treating agent of which main components are boric acid and borax is prepared by dissolving boric acid and borax in, for instance, purified water, distilled water or the like to form an aqueous solution.

In the present invention, the blending ratio of boric acid and borax is usually adjusted so that boric acid/borax (weight ratio) is 7/1 to 50/1, preferably 12/1 to 35/1. When the blending ratio of boric acid and borax is without the above range, the pH of an obtained treating solution is without the range of pH 6 to 7.5 which is equal to the pH of tear fluid even though citric acid and/or sodium citrate ($Na_3C_6H_5O_7$) is added thereto as a chelating agent explained later.

Also, it is desirable that the concentration of the treating agent in the aqueous solution containing a treating agent mainly composed of boric acid and borax is adjusted to usually 1 to 2.2 w/v %, preferably 1 to 1.8 w/v %. When the concentration of the treating agent exceeds 2.2 w/v %, the osmotic pressure exceeds 330 mmol/kg, and thereby eyes are sometimes stimulated when a soft contact lens treated with the solution is worn in the eyes. When the concentration of the treating agent is less than 1.5 w/v %, it is desirable to adjust the osmotic pressure of an obtained treating solution by adding a chelating agent explained later since the osmotic pressure is lower than 250 mmol/kg. When the concentration of the treating agent is less than 1 w/v %, there is a tendency that the osmotic pressure of an obtained treating solution cannot be adjusted to at least 250 mmol/kg even though the amount of the chelating agent is adjusted to the maximum. The reason why the osmotic pressure of the treating solution is adjusted to 250 to 330 mmol/kg is that the osmotic pressure can be equal to the osmotic pressure of tear fluid so that stimulation and the like are not given to eyes.

A chelating agent can be added to the treating agent mainly composed of boric acid and borax to sequester metallic ions contained in tear fluid, which impart wrong influences to a soft contact lens. As representative examples of a chelating agent, for instance, citric acid, sodium citrate ($Na_3C_6H_5O_7$), and the like are cited. It is desirable that the amount of the chelating agent is adjusted so that the chelating agent is contained in the treating solution in an amount of at most 1 w/v %, preferably 0.2 to 0.6 w/v %. When the amount of the chelating agent exceeds 1 w/v %, the electric conductivity of an obtained treating solution sometimes exceeds 8 mS/cm, and it tends to be difficult that the treating solution is mechanically distinguished from generally used soaking solutions for soft contact lenses by means of a simple apparatus. Also, for instance, thimerosal, paraben and the like can be suitably added to the treating agent as occasion demands for the sake of disinfecting.

It is desirable that the concentration of an electrolyte in the treating solution is 0.001 to 0.5 mol/l, preferably 0.05 to 0.2 mol/l, more preferably 0.1 to 0.2 mol/l. When the concentration is less than the above range, there is a tendency that high voltage should be applied to the solution so that an electric current is adjusted to generate peroxides. Also, when the concentration exceeds the above range, the osmotic pressure of the treating solution becomes too high, and thereby the size of a lens is deformed and there is a tendency that eyes are stimulated when the lens is treated with the treating solution and then the treated lens is worn in eyes as it is.

Also, since the electric charge of proteins in the treating solution is changed by the pH of the treating solution, the proteins sometimes do not move at all according to the pH of the treating solution. At that time, the pH is called as an isoelectric point (hereinafter referred to as pI) of the proteins. It is desirable that the pH of the treating solution used in the present invention is different from each pI of the proteins which are substantially main constituting components of tear fluid, such as albumin (pI 4.7 to 5.0), globulin (pI 5.2 to 5.4) and lysozyme (pI 10.5 to 11.4) for the sake of revelation of effects. That is, it is desirable that the treating solution has pH 1 to 4.6, pH 5.5 to 10.4 or pH 11.5 to 14. Further, in consideration of wrong influences to the material of a lens and safety for eyes when the lens is taken out from the treating solution after the treatment and then the lens is worn in eyes as it is, it is desirable that the treating solution has preferably pH 5.5 to 8, more preferably pH 6 to 7.5.

Further, in the present invention, one or more compound which does not generate hypohalogenous acid salts by electrolysis selected from the group consisting of urea, thiocyanic acid salts and compounds having reducing properties can be contained in the treating solution.

These compounds are the components for easily removing proteins existing in a lens, particularly denatured proteins which cannot be removed by usual electrophoresis. The function and amount of urea and thiocyanic acid salts are different from those of the compounds having reducing properties as mentioned later.

In general, urea and thiocyanic acid salts are components having a function to heighten the water solubility of low molecular nonelectrolytes, proteins and the like. According to the present invention, proteins adhered to the surface of a lens or proteins immanent in the lens are efficiently removed by multiplier action of the above function and removing function of proteins based upon electrophoresis and peroxides produced by electrode reaction. In general, there is a necessity to adjust the concentration of urea and/or thiocyanic acid salts in the treating solution relatively high to 0.5 to 4 mol/l, or so when an electric current is not charged to the solution to clean a lens thoroughly, but according to the present invention, since multiplier action together with peroxides and the like are exhibited as mentioned above, the concentration can be lowered to at most 0.5 mol/l, preferably 0.01 to 0.5 mol/l more preferably 0.04 to 0.06 mol/l or so. Also, there is a necessity to adjust the concentration to at least 0.01 mol/l so that the urea and/or thiocyanic acid salts can show the removing effect of proteins. Even when the concentration is lower than the above range, stains due to proteins adhered to a lens while the lens has been usually worn in eyes can be removed by the peroxides. Also, when the above concentration exceeds the above range, the removing effect of proteins is improved, but eyes smart with a lens when the lens is treated with the solution and then is worn in the eyes as it is since the osmotic pressure of the treating solution becomes relatively high.

As mentioned above, when urea and/or thiocyanic acid salts are used, since these can be used in a lower concentration, a lens would not be swollen or shrunk like a high concentration solution is used.

As concrete examples of the thiocyanic acid salts, for instance, ammonium thiocyanate, sodium thiocyanate, potassium thiocyanate, calcium thiocyanate, and the like can be cited, and these are used alone or by a combination of at least two of them.

The compounds having reducing properties used in the present invention have a nature for reducing intermolecular or intramolecular S—S bonds of proteins adhered to the surface of the lens or proteins immanent in the lens. When the compounds having reducing properties are used, it is desirable that the concentration in the treating solution is adjusted to usually at most 0.1 mol/l, preferably 0.005 to 0.05 mol/l. When the concentration exceeds the above range, removing effects of proteins improve. However, since the osmotic pressure of the electrolyte solution relatively becomes high, there is a tendency that the size of a treated lens is changed and eyes smart with a treated lens when the treated lens is worn in eyes as it is after the treatment.

As concrete examples of the compounds having reducing properties, for instance, thiosulfuric acid alkali metal salts or thiosulfuric acid alkaline earth metal salts such as sodium thiosulfate, potassium thiosulfate and calcium thiosulfate; sugars such as D-glucose, L-glucose, lactose and D-fructose; cysteine; methionine; acids, or alkali metal salts or alkaline earth metal salts thereof such as sorbic acid, potassium sorbate, citric acid and sodium citrate; sulfurous acid salts such as sodium sulfite, potassium sulfite and sodium hydrogen sulfite; ascorbic acid; glutathione, and the like are cited, and these compounds having reducing properties are used alone or by a combination of at least two of them. Also, according to the present invention, as mentioned above, urea, thiocyanic acid salts and compounds having reducing properties are usually used alone or by a combination of at least two of them. When urea and/or thiocyanic acid salts, and the compounds having reducing properties are simultaneously used, each amount of these can be within a range mentioned above, respectively.

The treating solution for soft contact lenses of the present invention can be an aqueous solution of the above treating agent beforehand prepared, or an aqueous solution which is prepared by dissolving the treating agent having a shape like powder, granules or pellets in water when a user uses the solution.

In the present invention, cleaning and disinfecting are carried out by immersing a lens in the treating solution and applying an electric current to the solution. As an electrode, it is desirable that the followings are used.

As an electrode material used in an anode, for instance, noble metals such as gold and platinum, a synthetic resin or ceramic on which gold or platinum is coated by plating or vacuum evaporating and the like are cited. As a material used in a cathode, any materials usually used as an electrode can be used without limitation, and for instance, carbon rod, metals such as stainless steel, platinum, gold, copper and nickel, a synthetic resin or ceramic on which gold, platinum or the like is coated by plating or vacuum evaporating and the like are cited. As to the anode, it is desirable that at least the surface of the anode is covered with gold, platinum or the like so that the electrode is not dissolved during electrolysis at the anode.

Also, when both of the electrodes are used without the change of anode and cathode, the above materials can be respectively used. When both of the electrodes are used as anode and cathode mutually, platinum or a synthetic resin or ceramic on which platinum is coated by plating or vacuum evaporating is desirable as the material of the electrodes from the viewpoints that the ionization tendency of these electrodes is small, thereby these materials would be little dissolved in the treating solution when an electric current is applied to the electrodes, and after the cleaning and disinfecting treatment, these materials act as a catalyst for completely decomposing peroxides generated in the treating solution during the application of an electric current.

In the present invention, the concentration of peroxides generated which are effective for removing proteins existed in a lens is suitably adjusted in accordance with the degree of stains of the lens by adjusting a current value applied to the treating solution and applying period of time of the electric current.

It is desirable that an electric current applied to the treating solution is 0.1 to 5 A, and more preferably 0.2 to 0.5 A so that stains such as proteins which are adhered to a lens during usual wearing can be removed. When the electric current is less than 0.1 A, peroxides are little generated in the electrolyte solution when an electric current is applied to the solution, thereby there is a tendency that the removing effects of proteins become small. When the electric current exceeds 5 A, the electrode reaction becomes radial on the electrodes, thereby the electrodes are sometimes damaged although the removing effects of proteins are not changed a little.

In the above treatment, it is desirable that the current density is 0.02 to 0.88 $A/cm^2$, preferably 0.04 to 0.09 $A/cm^2$ when an electric current is charged to the solution. When the current density is less than the above-mentioned range, there is a tendency that the temperature of the solution would not be increased rapidly. When the current density exceeds the above-mentioned range, overcurrent unnecessary for increasing the temperature of the solution flows in the solution, thereby the electrodes are sometimes damaged.

Also, the applying period of time of an electric current should be determined in consideration of boiling and disinfection of a lens since the temperature gradient changes in accordance with the amount of the treating solution. When the boiling and disinfection necessitate 10 minutes at 100° C., for instance, under the condition that an electric current is less than 0.3 A in 10 ml of the treating solution, the applying period of time of an electric current is desirably 15 to 30 minutes or so, and under the condition that an electric current is at least 0.3 A in that solution, the applying period of time of an electric current is desirably 1 1 to 15 minutes or so.

Also, it is desirable that the temperature of the treating solution is kept at 80° to 100° C. in view of heating and disinfecting a lens.

The temperature of the treating solution increases sufficiently when a direct current is merely applied to the solution within a range of the desirable current density aforementioned, but the increase of the temperature of the electrolyte solution may be promoted by using an auxiliary heating means such as a heater, for example.

Most of stains such as lipid adhered to a lens can be removed by boiling the lens in the treating solution. In order to remove the stains more sufficiently, the lens may be cleaned in a cleaning solution containing a surface active agent before putting the lens in a treating vessel or after cleaning and disinfecting the lens, or a surface active agent may be contained in the treating solution. As concrete examples of the surface active agent, for instance, anionic surface active agents such as surf uric acid esters of higher alcohols or liquid fatty acids, alkyl ether sulfuric acid esters, alkyl sulfonates and sulfosuccinates; cationic surface active agents such as alkyl amine salts and alkyl ammonium salts; nonionic surface active agents such as alkyl ethers, alkyl phenyl ethers, polyoxypropylene ethers, alkyl ester glycerine fatty acid esters, sorbitan fatty acid esters and polyoxyethylene sorbitan fatty acid esters are cited.

When the surface active agent is used by including in the treating agent, it is desirable that the concentration of the surface active agent in the treating solution is adjusted to at most 0.1% by weight, preferably at most 0.05% by weight since if the concentration of the surface active agent is too high, excess bubbles are generated in the treating solution and flow out from a vessel due to the gas generated during electrolysis.

Also, when denatured proteins are existed in the internal of a lens, a proteolytic enzyme can be included in the treating solution so that denatured proteins can be easily removed by applying an electric current.

As concrete examples of a proteolytic enzyme, for instance, vegetable proteolytic enzymes and animal proteolytic enzymes such as papain, chymopapain, pancreatin, trypsin, chymotrypsin, pepsin, ficin, carboxypeptidase, aminopeptidase and bromelin; proteolytic enzymes derived from microbes such as Bacillus, Streptomyces bacteria and Aspergillus mold, and the like are cited.

It is desirable that the concentration of the proteolytic enzyme is adjusted so that the enzyme activity of the proteolytic enzyme in the electrolyte solution is 300 to 1000 unit/ml.

In carrying out the method of the present invention, gels or membranes can be provided between electrodes and a lens so that the lens is insulated from the electrodes to capture proteins removed from the lens by an electric current. In this case, the gels or membranes play a role in insulation between the electrodes and the lens, and an electric current is applied to the gells or membranes by passing through the treating solution impregnated in the gells or membranes. As materials of the gells or membranes, for instance, filter paper, silica gel, cellulose powder, porous sponge rubber, cellulose acetate, polyacrylamide gel, polyvinylalchol gel, nitrocellulose membrane, and the like are cited.

The thus cleaned and disinfected lens can be worn in eyes after the lens is taken out from the electrolyte solution as it is or after the lens is cleaned with a saline solution if the electrolyte solution gives stimulation to eyes.

According to the method for cleaning and disinfecting of the present invention, since hypohalogenous acid salts are not generated when an electric current is applied to the treating solution, there is no apprehension of discoloration or decoloration of a colored lens and stimulation such as smarting of eyes is not generated, and further, proteins adhered on or incorporated in a lens can be removed by excellent detergency, and at the same time the lens can be thermally disinfected.

Also, as mentioned above, since the treating solution for soft contact lenses containing a treating agent mainly composed of boric acid and borax has an electric conductivity (at most 8 mS/cm) smaller than the electric conductivity of conventional treating solutions for soft contact lenses (10 to 15 mS/cm), the misuse of the solution can be avoided by detecting the difference of current value between the treating solution according to the present invention and conventional treating solutions for soft contact lenses. Also, since the treating solution for soft contact lenses of the present invention has pH 6 to 7.5 and an osmotic pressure of 250 to 330 mmol/kg which are equal to those of tear fluid, the treating solution is excellent in safety for eyes.

Next, the present invention is explained more specifically on the basis of examples. However, the present invention is not limited to only the examples.

REFERENTIAL EXAMPLE 1

To 9 ml of a citric acid salt buffer solution (pH 6.8) having a sodium citrate concentration of 0.075 mol/l and a citric acid concentration of 0.005 mol/l, voltage of 60 V and an initial current of 0.2 A were applied. The concentration of peroxides in the buffer solution with the passage of time of application of electricity was measured in accordance with the following method. The result is shown in FIG. 1.

Method for Measuring the Concentration of Peroxides

First of all, reagents were prepared by the following method.

(A) Phosphoric acid salt buffer solution: After 0.07 mol of sodium phosphate (special grade chemical) and 0.13 mol of disodium phosphate (special grade chemical) were dissolved in distilled water and pH was adjusted to 7.0, distilled water was added thereto to give a total amount of 1 l of a buffer solution.

(B) ABTS reagent: To the above phosphoric acid salt buffer solution, 0.113 9 of 2,2'-azinobis(3-ethylbenzothiazoline-6-sulfonic acid) $2NH_4$ salt (ABTS special grade chemical) and 100 units of PEROXIDASE from Horseradish Type I (commercially available from SIGMA CHEMICAL COMPANY, trade name) were added to give a total amount of 100 ml of an ABTS reagent.

(C) Next, after 2.0 ml of hydrogen peroxide standard solution which was diluted to at most 30 ppm and 2.0 ml, of the above ABTS reagent solution were admixed and stirred, ultraviolet ray absorbance (hereinafter referred to as absorbance) was measured at 420 nm. An analytical curve was prepared by measuring the absorbance at every concentration.

Next, 2.0 ml of samples were collected from the electric-current flowed citric acid salt buffer solution at hourly intervals. After the sample was mixed with 2.0 m l of the ABTS reagent solution and stirred, the absorbance at 420 nm was measured. Then, the concentration converted to a concentration of hydrogen peroxide was measured from the analytical curve.

As shown in FIG. 1, the concentration of peroxides in the buffer solution increased just before boiling (about 2 minutes passed from the begining of the application of an electric current), and after that the concentration decreased. When 7 minutes passed from the beginning of the application of an electric current, the concentration became nearly 0 ppm.

That is, since peroxides dangerous for eyes are not existed in the solution, the lens is safe for eyes even though the lens is taken out from the solution and worn in eyes as it is.

REFERENTIAL EXAMPLES 2 TO 5

In the same manner as that described in Referential Example 1, instead of a citric acid salt buffer solution, a 0.2 mol/l, phosphoric acid salt buffer solution (Referential Example 2), a 0.3 mol/l of boric acid salt buffer solution (Referential Example 3), a 0.1 mol/l sodium sulfate aqueous solution (Referential Example 4) or a 0.08 mol/l sodium hydrogencarbonate aqueous solution (Referential Example 5) was used, and to 9 ml of which the voltage of 60 to 90 V and an initial electric current of 0.2 A were applied. The concentration of peroxides in each electrolyte solution was measured in the same manner as that described in Referential Example 1.

As to each of the electrolyte solutions, after 2 to 6 minutes passed from the beginning of the application of an electric current, peroxides were generated as well as in Referential Example 1. After boiling, the concentration of the peroxides decreased.

REFERENTIAL EXAMPLES 6 AND 7, AND COMPARATIVE REFERENTIAL EXAMPLE 1

A buffer solution of boric acid-EDTA described in U.S. Pat. No. 4,732,185, that is, a buffer solution composed of 0.808 mol/l boric acid, 0.029 mol/l EDTA and 0.825 mol/l tris(hydroxymethyl) aminomethane was prepared. The osmotic pressure of the buffer solution was 785 mmol/kg. In each of the boric acid-EDTA buffer solution (Comparative Referential Example 1), the citric acid salt buffer solution (osmotic pressure 260 mmol/kg) used in Referential Example 1 (Referential Example 6) and a saline solution (osmotic pressure 290 mmol/kg) (Referential Example 7), a soft contact lens mainly composed of N-vinylpyrrolidone and N,N-dimethylacrylamide having a water content of 72% (lens size at 20° C.: 13.5 mm) was immersed respectively. After 20 minutes passed, the lens size at 20° C. was measured. As a result, each lens which was immersed in the saline solution and the citric acid salt buffer solution had a size of 13.5 mm, respectively. To the contrary, the lens which was immersed in the boric acid-EDTA buffer solution had a lens size of 12.5 mm. Accordingly, the boric acid-EDTA buffer solution has great influence on a lens.

REFERENTIAL EXAMPLE 8 AND COMPARATIVE REFERENTIAL EXAMPLE 2

Electric properties of proteins (in particular lysozyme) were examined by an electrophoresis method (disk method) in accordance with the following procedures.

(A) The following acrylamide gel solution was prepared.

| (Components) | (Mixing amount) |
|---|---|
| (Solution A) | |
| 1N KOH | 8 ml |
| Glycine | 19 g |
| N,N,N',N'-tetramethylethylenediamine | 0.077 ml |
| Distilled water | An amount to give a total amount of 100 ml (pH 7.3) |
| (Solution B) | |
| Acrylamide | 60 g |
| N,N'-methylenebisacrylamide | 0.4 g |
| Distilled water | An amount to give a total amount of 100 ml |
| (Solution C) | |
| Ammonium persulfate | 0.14 g |
| Distilled water | An amount to give a total amount of 100 ml |

(B) Preparation of a 30% gel (corresponding to a lens having a water content of 70%)

A gel column was prepared by polymerizing acrylamide in a glass tube.

Firstly, a glass tube (internal diameter 5 mm, length 60 mm) was vertically stood on a table with a rubber stopper.

Next, the above solution A, solution B and solution C were mixed together so that solution A:solution B:solution C was 1:2:1 (weight ratio), and the mixed solution was poured into the above glass tube with a pipette so that bubbles were not generated. The solution was poured into the glass tube up to about 10 mm from the top end of the glass tube. Then, distilled water was gently poured into the glass tube with a pipette having a fine tip up to about 5 mm from the top end of the glass tube. The distilled water was poured so that acrylamide was separated from air and gelation could be easily proceeded. In that condition, the glass tube was allowed to stand for about one hour at room temperature (22° C.) to give a gel of acrylamide in the glass tube.

(C) Electrophoresis

Figure 2:
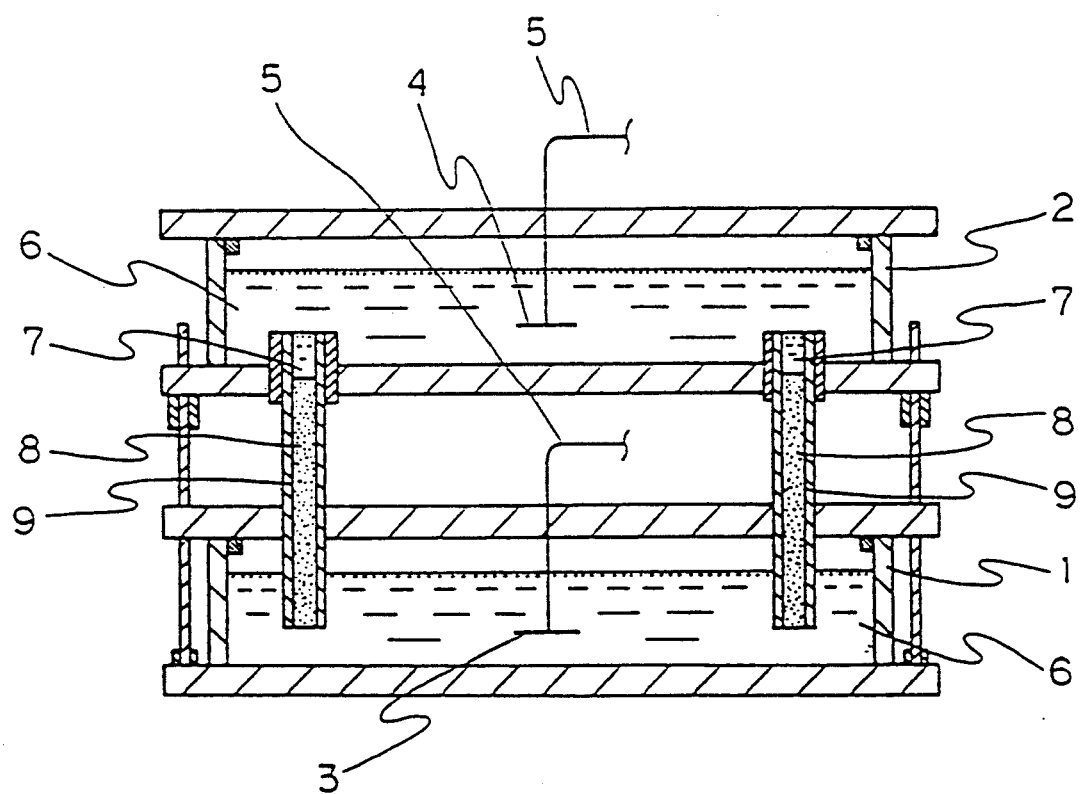
FIG. 2 is a schematic illustrative drawing of an apparatus for examining electrophoresis of proteins in Referential Example 8 of the present invention and Comparative Referential Example 2.

The electrophoresis is explained based upon FIG. 2.

A treating vessel 1 equipped with a platinum cathode 3 (area of electrode plate: 0.79 cm$^2$) which was connected to a direct current power source via a lead wire 5 was filled with 150 ml of a 0.3 mol/l boric acid salt buffer solution used in Referential Example 3 as an electrolyte solution 6. Also, in the same manner as that described above, a treating vessel 2 equipped with a platinum anode 4 (area of electrode plate: 0.79 cm$^2$ which was connected to the direct current power source via a lead wire 5 was filled with 150 ml of the buffer solution which was the same as that used in the treating vessel 1.

An amount 0.03 ml of a sample 7 prepared by dissolving 0.3 g of lysozyme in 5 ml of a 20% sucrose aqueous solution was poured on a gel 8 in a glass tube to give a gel column 9.

The treating vessels 1 and 2 were connected together with two gel columns 9 so that the treating vessel 2 was mounted on the treating vessel 1. While the electrolyte solution 6 in each treating vessel was kept at 20° to 22° C., an electric current of 3 mA was applied per one gel column 9 for one hour.

Next, the gel columns 9 were removed from the treating vessels 1 and 2, and the gel 8 was taken out from the glass tube with a needle. The gel was immersed in a 7% acetic acid aqueous solution of 1% by weight of Amide Black 10B (first grade class chemical) for one hour to dye the gel in whole (Referential Example 8).

As another sample 7, sucrose solution of lysozyme was thermally denatured by boiling for 10 minutes and an undissolved cloudy solution was obtained. The same procedure as that described above was carried out except that 0.03 ml of the undissolved cloudy solution was used, and after an electric current was applied to the solution in the same manner as that mentioned above, a gel 8 was dyed in the same manner as that mentioned above (Comparative Referential Example 2).

Since the color of each dyed gel was uniformly dark blue, excess Amide Black 10B was removed by washing the gel with a 7% acetic acid aqueous solution to sufficiently decolor the gel. After that, only the portion of lysozyme was distinguished.

As a result, as to Referential Example 8, since the gel was not decolored up to about 37 mm from the top end of the gel, it could be seen that lysozyme moved in the gel during the application of an electric current. To the contrary, as to Comparative Referential Example 2, since all portions of the gel were decolored, it could be seen that lysozyme was not moved in the gel when an electric current was applied to the solution. That is, it could be seen that denatured proteins were not entirely removed by electrophoresis.

EXAMPLE 1

About 1 l of an artificial tear fluid (pH 7.0) was prepared by mixing the following components.

Two soft contact lenses mainly composed of N-vinylpyrrolidone having a water content of about 70% were immersed in 1.5 ml of the artificial tear fluid at 37° C. for 16 hours to adsorb proteins in the lens.

Ingredients of the Artificial Tear Fluid

| | |
|---|---|
| Albumin | 3.88 g |
| γ-Globulin | 1.61 g |
| Lysozyme | 1.2 g |
| NaCl | 9.0 g |
| $CaCl_2.2H_2O$ | 0.15 g |
| $NaH_2PO_4.2H_2O$ | 1.04 g |
| Distilled water | 1.0 l |

Next, after one of the above lenses was washed by fingers with a cleaning agent for soft contact lenses MENI CLEAN (commercially available from Menicon Co., Ltd., trade name), the lens was immersed in 9 ml of a citric acid salt buffer solution (pH 6.8) having a sodium citrate ($Na_3C_6H_5O$) concentration of 0.075 mol/l and a citric acid concentration of 0.005 mol/l, and voltage of 60 V and an initial electric current of 0.2 A (current density: 0.04 A/cm$^2$) were applied thereto. After 3 minutes passed from the beginning of the application of the electric current, the temperature of the solution attained to 100° C. During the electrolysis, the current value increased to 0.45 A (current density: 0.08 A/cm$^2$), and after the temperature of the solution attained to 80° C., the current value lowered to 0.15 A (current density: 0.03 A/cm$^2$).

After the electric current was applied to the solution for 13 minutes, the solution was allowed to stand to cool to room temperature (22° C.). The above procedure (from the procedure of immersing a lens in 1.5 ml of the artificial tear fluid to the procedure of cooling) was counted as one cycle (hereinafter referred to cycle test $A_1$). After the above procedure was applied to a lens 100 cycles, when the lens was observed with naked eyes, the lens had transparency quite equal to a lens to which cycle test $A_1$ was not applied.

Further, the cross section of a lens was analyzed by an X-ray microanalyzer (commercially available from JEOL Co., JSM type 35) to examine the existence of sulfur after the cycle test $A_1$ was carried out 100 cycles. As a result, the existence of sulfur was not observed in the above treated lens.

COMPARATIVE EXAMPLE 1

In the same manner as that described in Example 1, after a soft contact lens was immersed in the above artificial tear fluid and the lens was washed by fingers with MENI CLEAN, the lens was disinfected in 1.5 ml of a soaking solution for soft contact lenses MENI SOAK (commercially available from Menicon Co., Ltd., trade name) by using MENICON LIZER E (hereinafter referred to as LIZER E) as an apparatus for boiling and disinfecting a soft contact lens.

In the same manner as that described in Example 1 except that a lens was treated with LIZER E instead of the application of an electric current, a cycle test (hereinafter referred to as cycle test $B_1$) was carried out 100 cycles. After the cycle test $B_1$ was carried out about 40 cycles, it was observed with naked eyes that the lens disinfected with LIZER E became cloudy.

Next, in the same manner as that described in Example 1, the cross section of the lens was analyzed with an X-ray microanalyzer to observe the existence of sulfur. As a result, a peak showing the existence of sulfur was detected in the lens treated with LIZER E.

Since the lens material does not contain sulfur inherently, it is supposed -that the detected sulfur is derived from the molecular structure of proteins, and the denatured proteins causes the cloudiness of the lens.

On the other hand, since sulfur was not detected from the lens to which the cycle test $A_1$ was applied, it can be seen that the cleaning and boiling of a lens can be continuously carried out when an electric current is applied in such a manner as in Example 1.

Further, the cycle test $B_1$ was carried out by using a citric acid salt buffer solution (pH 6.8) which was the same as that used in Example 1 instead of MENI SOAK. After the cycle test $B_1$ was carried out about 40 cycles, it was observed with naked eyes that the lens became cloudy.

That is, when an electric current is applied, the cleaning of a lens can be finished for the first time.

EXAMPLE 2 AND COMPARATIVE EXAMPLE 2

A used cloudy lens was divided into three pieces. After two of the pieces were observed in a dark field with a microscope, respectively, the one was dipped in 9 ml of the citric acid salt buffer solution used in Example 1 and voltage of 60 V was applied thereto for 4 minutes. The initial electric current was 0. 2 A (current density: 0.04 A/cm$^2$) (Example 2). After 3 minutes passed from the beginning of the application of an electric current, the temperature of the solution attained to 100° C. During the electrolysis, the current value increased to 0.45 A (current density: 0.08 A/cm$^2$), and after the temperature of the solution attained to 80° C., the electric current lowered to 0.15 A (current density: 0.03 A/cm$^2$).

Another piece was dipped in 9 ml of the same citric acid salt buffer solution as the above and the buffer solution was boiled for 10 minutes (Comparative Example 2).

After the treatments, when the above two pieces of the lens were observed in a dark field with a microscope, stains of the one which was treated with an electric current (Example 2) were almost removed, but stains of another which was boiled in the citric acid salt buffer solution were not entirely removed.

From the above results, peroxides generated by an electric current are effective for removing denatured and undissolved proteins.

COMPARATIVE EXAMPLE 3

After remained one of three pieces of the returned cloudy lens divided in Example 2 and comparative Example 2 was observed in a dark field with a microscope, the piece was dipped in an agent for removing proteins HYDROCARE®-F (SANTEN-ALLERGAN, trade name) for 4 minutes.

After the lens piece was dried, when the piece was observed in a dark field with a microscope, no stains were almost removed from the piece.

That is, as is clear from the comparison with Example 2 in which a treatment was carried out in the same time (4 minutes), it can be seen that the treatment in Example 2 of the present invention can remove stains for an extremely shorter time.

EXAMPLE 3

Four soft contact lenses mainly composed of N-vinylpyrrolidone having a water content of about 70% were immersed in 1.5 ml of an artificial tear fluid composed of the following components at 37° C. for one hour.

Ingredients of the Artificial Tear Fluid

| | |
|---|---|
| Albumin | 11.64 g |
| γ-Globulin | 4.83 g |
| Lysozyme | 3.6 g |
| NaCl | 9.0 g |
| $CaCl_2 \cdot 2H_2O$ | 0.15 g |
| $NaH_2PO_4 \cdot 2H_2O$ | 1.04 g |
| Distilled water | 1.0 l |
| | (pH 7.0) |

Next, after two of the above lenses were cleaned by fingers with NENI CLEAN, the lenses were immersed in 12 ml of a 0.05 mol/l phosphoric acid salt buffer solution containing 0.2 mol/l of urea (pH 6.8), and voltage of 100 V was applied to the solution for 8 minutes. The initial current was 0.8 A (current density 0.11 $A/cm^2$). After 2 minutes passed, the temperature of the solution attained to 100° C. During that procedure, the current value increased up to 1.0 A (current density: 0.13 $A/cm^2$). After the temperature of the solution attained to 80° C., the current value lowered to 0.2 A (current density 0.03 $A/cm^2$). The solution was allowed to stand to cool to room temperature.

Next, the above procedure was counted as one cycle (hereinafter referred to cycle test $A_2$). After the procedure was applied to the lenses 100 cycles, the lenses were observed with naked eyes. As a result, the lenses had quite the same transparency as the lens which was not treated by the cycle test $A_2$.

Further, when the cycle test $A_2$ was applied to the lenses 100 cycles, and then the existence of sulfur and phosphorus was examined by an X-ray microanalyzer, none of sulfur and phosphorus were detected.

That is, since the two lenses were transparent after the cycle test $A_2$ was applied to the lenses 100 cycles, it can be seen that both of the disinfection due to boiling and the removal of proteins were carried out when an electric current was applied to the solution.

COMPARATIVE EXAMPLE 4

After two remained lenses of four lenses which were treated with the artificial tear fluid were cleaned by fingers with MENI CLEAN, the lenses were boiled in 1.5 ml of MENI SOAK with LIZER E.

Hereinafter, a cycle test (boiling was carried out using LIZER E instead of applying an electric current (hereinafter referred to as cycle test $B_2$)) was carried out 100 cycles. As a result, it became obvious by naked eyes that the lenses were cloudy after the cycle test $B_2$ was applied to the two lenses boiled in LIZER E about 20 cycles. Further, after the cycle test $B_2$ was carried out 100 cycles, the existence of sulfur and phosphorus was examined by an X-ray microanalyzer. As a result, a peak showing the existence of sulfur was detected.

That is, it is supposed that the cloudiness of this lens was caused by proteins, and when the lens was not electrically boiled, it can be seen that proteins are accumulated in the lens.

Also, a peak showing the existence of phosphorus was not detected.

EXAMPLES 4 TO 12

Instead of a 0.05 mol/l phosphoric acid salt buffer solution (pH 6.8) containing 0.2 mol/l of urea used in Example 3 as an electrolyte solution, an electrolyte solution containing a component having a concentration shown in Table I was used and the cycle test $A_2$ was applied 100 cycles to the same lenses as those used in Example 3 in the same manner as that described in Example 3. Next, the transparency of the lenses were compared with the lenses which were not treated by the above cycle test $A_2$ with naked eyes. The results are shown in Table 1.

TABLE 1

| Ex. No. | Kind and concentration of urea, thiocyanic acid salt and/or compound having reducing property contained in electrolyte solution | | | Electrolyte in electrolyle solution and concentration thereof | | Transparency of lens after 100 cycles |
|---|---|---|---|---|---|---|
| 4 | Urea | 0.2 | mol/l | Sodium sulfate | 0.035 mol/l | Transparent |
| 5 | Urea | 0.2 | mol/l | Ammonium sulfate | 0.038 mol/l | " |
| 6 | Urea | 0.2 | mol/l | Sodium acetate | 0.061 mol/l | " |
| 7 | Sodium sulfite | 0.03 | mol/l | Sodium dihydregenphosphate | 0.025 mol/l | " |
| | | | | Disodium hydrogenphosphate | 0.025 mol/l | |
| 8 | Sodium sulfite | 0.05 | mol/l | Sodium dihydregenphosphate | 0.025 mol/l | " |
| | | | | Disodium hydrogenphosphate | 0.025 mol/l | |
| 9 | Cysteine | 0.005 | mol/l | Sodium dihydregenphosphate | 0.025 mol/l | " |
| | Sodium sulfite | 0.04 | mol/l | Disodium hydrogenphosphate | 0.025 mol/l | |
| 10 | Cysteine | 0.01 | mol/l | Sodium dihydregenphosphate | 0.025 mol/l | " |
| | Sodium sulfite | 0.04 | mol/l | Disodium hydrogenphosphate | 0.025 mol/l | |
| 11 | Cysteine | 0.005 | mol/l | Sodium dihydregenphosphate | 0.025 mol/l | " |
| | Sodium sulfite | 0.02 | mol/l | Disodium hydrogenphosphate | 0.025 mol/l | |
| | Sodium thiocyanate | 0.02 | mol/l | | | |
| 12 | Urea | 0.1 | mol/l | Sodium dihydregenphosphate | 0.025 mol/l | " |
| | | | | Disodium hydrogenphosphate | 0.025 mol/l | |

As is clear from the results shown in Table 1, it can be seen that both of the disinfecting treatment due to boiling and removal of proteins were carried out as to any of the lenses to which the cycle test $A_2$ was applied 100 times in Examples 4 to 12. Also, although the existence of sulfur and phosphorus in the section of the lenses was examined with an X-ray microanalyzer in the same manner as in Example 3, sulfur and phosphorus were not detected in any of the lenses used in Examples 4 to 12.

EXAMPLE 13

After two lenses which were similar to those used in Example 3 were immersed in 1.5 ml of the same artificial tear fluid as that used in Example 3 at 37° C. for one hour, and the lenses were washed by fingers with MENI CLEAN, the lenses were disinfected in 1.5 ml of a 0.05 mol/l phosphoric acid salt buffer solution (pH 6.8) containing 0.2 mol/l of urea with LIZER E. Next, the above two lenses were allowed to stand to cool to room temperature.

The above procedure was counted as one cycle, and the procedure was applied to the above two lenses 50 cycles. When the lenses were observed with naked eyes, both lenses became cloudy after the above procedure was carried out 10 times or so.

As is clear from the above result, it can be seen that proteins cannot be removed from lenses when the disinfecting treatment with the above LIZER E is carried out.

Further, one of the clouded lenses was immersed in 12 ml of a 0.05 mol/l phosphoric acid salt buffer solution (pH 6.8) containing 0.05 mol/l of sodium sulfite after the above treatment was carried out 50 cycles, and voltage of 60 V was applied to the solution for 10 minutes. The initial current was 0.8 A (current density: 0.11 A/cm$^2$). After 2 minutes passed from the begining of the application of an electric current, the temperature of the solution attained to 100° C. During this treatment, the current value of this solution increased up to 1.0 A (current density 0.13 A/cm$^2$). After the temperature of the solution attained to 80° C., the current value lowered to 0.3 A (current density: 0.04 A/cm$^2$). After that, the lens was taken from the solution. When the lens was examined with naked eyes, the lens was recovered to transparency.

From the above results, it can be seen that even though proteins are fixly adhered to lenses due to thermal denaturation, the proteins can be removed from the lenses by immersing the lenses in an electrolyte solution and applying an electric current to the solution according to the method of the present invention.

EXAMPLE 14 AND COMPARATIVE EXAMPLE 5

To two of four soft contact lenses mainly composed of N-vinylpyrrolidine and N,N-dimethylacrylamide having a water content of 80%, the cycle test $A_2$ was applied 100 cycles in the same manner as that in Example 3 (Example 14), and to the other two lenses, a treatment was applied in the same manner as that in Comparative Example 4 (Comparative Example 5). After that, cloudiness of lenses were observed.

The two lenses electrically treated in Example 14 were transparent after the cycle test $A_2$ was carried out 100 cycles. To the contrary, it was observed that the two lenses thermally treated by boiling the lenses with LIZER E became cloudy after the treatment was carried out 30 cycles or so.

EXAMPLE 15 AND COMPARATIVE EXAMPLE 6

To two of our contact lenses mainly composed of N-vinylpyrrolidine and N, N-dimethylacrylamide having a water content of 72%, the cycle test $A_2$ was applied (Example 15), and to the other two lenses, a treatment was applied in the same manner as that in Comparative Example 1 (Comparative Example 6). After that, cloudiness of lenses were observed.

The two lenses electrically treated in Example 15 were transparent after the cycle test $A_2$ was carried out 100 cycles. To the contrary, it was observed that the two lenses thermally treated by boiling the lens with LIZER E became cloudy after the treatment was carried out 42 cycles or so.

EXAMPLE 16

Two soft colored contact lenses of OPTIMA 38 (commercially available from BAUSCH & LOMB INCORPORATED, trade mark) and HYDRON soft colored contact lens (commercially available from HYDRON JAPAN K.K., trade name: 114 Rodhos) were divided into two pieces with a razor's edge, respectively, and each one of the two pieces was stored in a saline solution. The remained pieces were immersed in 9 mg of the citric acid salt buffer solution (pH 6.8) used in Example 1, and voltage of 6 0 V and an initial current of 0. 2 A (current density: 0.04 A/cm$^2$) were applied thereto for 13 minutes. After 3 minutes passed from the beginning of the application of an electric current, the temperature of the solution attained to 100° C . During the treatment, the current value increased up to 0.45 A (electric density: 0.08 A/cm$^2$), and after the temperature of the solution attained to 80° C., the current value lowered to 0.15 A (current density: 0.03 A/cm$^2$). The treatment was repeated. However, the above buffer solution was exchanged for a new buffer solution per 13 minutes.

The pieces were electrically treated 365 times and taken out from the treating solution. The degree of discoloration of the pieces were examined by comparing with the pieces having the same kind as the above pieces stored in the saline solution As a result, the electrically treated pieces were not discolored at all. From the result, it could be seen that the method for cleaning and disinfecting according to the present invention could be sufficiently applied to soft colored contact lenses.

COMPARATIVE EXAMPLE 7

Two soft colored contact lenses of OPTIMA 38 used in Example 16 and HYDRON soft colored contact lens were divided into two pieces, respectively in the same manner as in Example 16, and each one of the two pieces was stored in a saline solution.

On the other hand, the remained pieces were immersed in 3.0 ml of an aqueous solution having a sodium citrate concentration of 0.019 mol/l, a citric acid concentration of 0.0003 mol/l and a sodium chloride concentration of 0.154 mol/l per 100 ml of distilled water having a temperature of about 20° C., an electric current of 0.006 A was applied thereto for 25 seconds with the same apparatus as that used in Example 1 to generate sodium hypochlorite having a concentration of about 5 ppm to disinfect. After the solution was allowed to stand for 60 minutes at room temperature as it is, the pieces were taken out, and the solution was exchanged for a new solution. The procedure was counted as one cycle, and the cycle was repeated 50 times.

The degree of discoloration or decoloration of the lenses were observed by comparing the color of the disinfected pieces with the color of the pieces stored in a saline solution in the same manner as that described above. As a result, the pieces of the soft colored contact lenses of BAUSCH & LOMB were completely decolored when the above procedure was only 2 times repeated. It was also observed that the pieces of the soft colored contact lens of HYDRON became discolored after the procedure was repeated 20 times.

From the above results, when a disinfecting system functioning hypohalogenous acid salts to soft colored contact lenses was employed, it could be seen that the soft colored contact lenses were discolored or decolored.

EXAMPLE 17

An amount 1.8 g of a granular treating agent composed of 72.2% by weight of boric acid, 3.3% by weight of borax and 24.5% by weight of sodium citrate was dissolved in 100 ml of purified water to give a treating solution for soft contact lenses.

This treating solution had pH 6.9 and an osmotic pressure of 255 mmol/kg.

Next, a soft contact lens "MENICON MA" (commercially available from Menicon Co. Ltd., trade mark) was immersed in this treating solution, and allowed to stand for 16 hours. After that, the size of the lens was measured. As a result, the size was 13.5 mm.

Next, voltage of 90 V and an initial current of 0.15 A were applied to the treating solution while the soft contact lens was immersed in 9 ml of the treating solution.

After the voltage was applied to the solution for 13 minutes, the soft contact lens was taken out therefrom. As a result, the blue color of the soft contact lens was not disappeared, and showed the same blue color as that of a contact lens to which any treatment was not applied. Therefore, it could be seen that the treatment does not affect the color of a lens at all.

Next, to the soft contact lens which was treated by immersing the lens in the above treating solution, the same procedure as that mentioned above was applied 365 times. The treating solution was exchanged for a new treating solution per the passage of 13 minutes.

After that, when the color of the lens was examined, the lens had the same blue color as a soft contact lens to which any treatment was not applied, and discoloration was not observed. Also, the size of the lens was 13.5 mm in the treating solution (temperature of the solution 20° C.), and no change was observed.

Also, when the electric conductivity of the treating solution was measured, the electric conductivity was 3.6 mS/cm.

COMPARATIVE EXAMPLE 8

Instead of the treating solution used in Example 17, a soaking solution for soft contact lenses MENI SOAK (commercially available from Menicon Co., Ltd., trade mark) was used. The soaking solution had pH 7.0 and an osmotic pressure of 290 mmol/kg.

When the same soft contact lens as that used in Example 17 was immersed in the soaking solution (the temperature of the solution 20° C.) and the lens size was measured in the same manner as that described in Example 17, the lens size was 13.5 mm.

Next, voltage of 40 V was applied to 9 ml of the soaking solution in which the soft contact lens was immersed. The initial current was 0.15 A.

After the voltage was applied for 13 minutes, the soft contact lens was taken out from the solution. As a result, the blue color of the soft contact lens disappeared and became transparent completely.

Also, when the electric conductivity of the soaking solution was measured, the electric conductivity was 14.4 mS/cm.

EXAMPLE 18 AND COMPARATIVE EXAMPLE 9

Four soft contact lenses mainly composed of N-vinylpyrrolidone and N,N-dimethylacrylamide having a water content of 72% were immersed in 1.5 ml of a 0.01 mol/l calcium chloride aqueous solution (containing calcium ion of 400 Ppm)p respectively, and the solution was boiled for 5 minutes.

After the solution was cooled to room temperature for approximately 15 minutes, the surface of each lens was rinsed with distilled water, and two of the lenses were dipped in 7 ml of a 0.03 mol/l phosphoric acid buffer solution (pH 7.0) to boil for 10 minutes (Comparative Example 9). Also, the remained two lenses were immersed in 7 ml of the above buffer solution to apply voltage of 90 V and an initial current of 0.15 A for 13 minutes (Example 18).

After cooling, each of the lenses was immersed again in the same calcium chloride aqueous solution as that mentioned above and boiled for 5 minutes, and a cycle of boiling two lenses in the buffer solution and applying an electric current to the other two lenses in the buffer solution was repeated.

As to the lenses to which the cycle test was applied in Comparative Example 9, when the cycle test was carried out 5 cycles, it was observed that the lenses became cloudy due to calcium phosphate, but as to the lenses to which the cycle test was applied in Example 18, the lenses were transparent after the cycle test was carried out 5 cycles.

As mentioned above, it is known that a metallic ion, particularly calcium ion forms a water insoluble salt together with carbonate ion, phosphate ion and the other components, thereby a lens becomes cloudy. To the contrary, according to the present invention, even though a lot of calcium ion is included in a lens, the ion can be removed.

EXPERIMENTAL EXAMPLE 1

Figure 3:
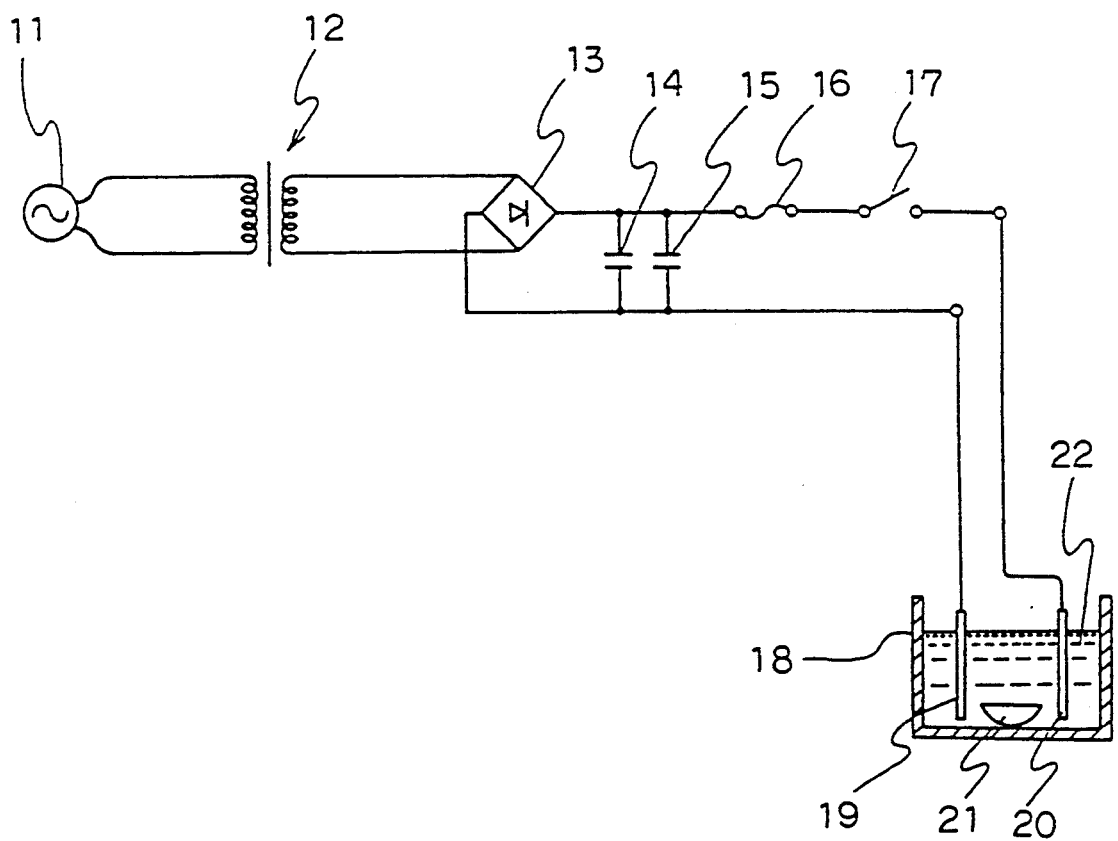
FIG. 3 is a schematic illustrative drawing of a cleaning apparatus used in Experimental Example 1.

A cleaning apparatus shown in FIG. 3 was used. In FIG. 3, 11 denotes a power supply (alternating current 100 V), 12 denotes a transformer for transforming 100 V of AC into 90 V of AC, 13 denotes a bridge rectifier (Standard: 400 V, 3 A), 14 and 15 denote aluminium solid electrolytic capacitor (Standard: 200 V, 470 $\mu$F) respectively, 16 denotes a fuse (Standard: 100 V, 0.3 A), 17 denotes a switch, 18 denotes an electrolytic bath, 19 and 20 denote platinum electrodes (area of electrode: 0.21 cm$^2$), and 21 denotes the same soft contact lens as that used in Example 17. Also, the interval of the platinum electrodes was adjusted to 3 cm.

The cleaning apparatus shown in FIG. 3 was used, and the electrolytic bath 18 was charged with 9 ml of the treating solution 22 obtained in Example 17 or the treating solution obtained in Comparative Example 8. When voltage of 90 V was applied to the solution, as to the treating solution obtained in Example 17, an electric current continued to flow, but as to the treating solution obtained in Comparative Example 8, the fuse was cut off the moment voltage was applied to the solution and an electric current was not flowed.

As the other soaking solutions, a soaking solution prepared by using TORAY TABLETS FOR SOAKING SOLUTION (commercially available from Toray Industries, Inc.) in accordance with an instruction manual, a soaking solution prepared by using Tap Soak ® granules (commercially available from SANTEN-ALLERGAN) in accordance with an instruction manual, PURE SOAK S (commercially available from Hoya Corporation), Saline Solution (commercially available from BAUSCH & LOMB INCORPORATION), MYTEAR (commercially available from SENJU PHARMACEUTICAL Co., LTD.), RINSE (commercially available from SEIKO CONTACTLENS INC), SOFRINSE (commercially available from SEED K.K.), or LENSRINS ® (commercially available from Ciba Vision Care Japan Co., Ltd.) was used. To 9 ml of each soaking solution, the same procedure as that mentioned above was applied. As a result, in each of the soaking solutions, a fuse was cut off the moment voltage was applied to the solution and an electric current was not flowed.

From the results described above, it can be seen that the treating solution of the present invention can be mechanically distinguished from conventional soaking solutions for soft contact lenses by using a simple device such as fuse.

For the reference, since pH, osmotic pressure and electric conductivity of the above conventional soaking solutions were measured, the results are shown in Table 2.

TABLE 2

| Kind of soaking solution | pH | Osmotic pressure (mmol/kg) | Electric Conductivity (mS/cm) |
|---|---|---|---|
| TABLETS FOR SOAKING SOLUTION | 6.85 | 269 | 13.7 |
| Tap Soak ® granules | 6.05 | 309 | 12.6 |
| PURE SOAK S | 7.25 | 309 | 13.4 |
| Saline Solution | 7.23 | 282 | 10.4 |
| MYTEAR | 7.25 | 279 | 12.6 |
| RINSE | 7.17 | 279 | 10.3 |
| SOFRINSE | 6.44 | 280 | 13.0 |
| LENSRINS ® | 7.18 | 291 | 12.5 |

EXPERIMENTAL EXAMPLE 2

Next, treating solutions composed of various components were prepared, and pH, osmotic pressure and electric conductivity thereof were measured. The results are shown in Table 3.

Industrial Applicability

The method for cleaning and disinfecting a lens of the present invention does not impart wrong influences to the material, regulation and shape of a lens nor necessitate a complex procedure. Further, according the method, proteins, metallic ions and the like can be removed in a short time by excellent detergency, and the lens can be disinfected at the same time stains are removed. Also, according to the method of the present invention, in case that the method is applied to a colored contact lens or a marked lens, the lens is not decolored nor discolored. Further, according to the method of the present invention, since harmful components do not remain in a lens after the treatment of a lens, the lens is extremely safe for eyes when the lens is worn in eyes.

The treating solution for a soft contact lens of the present invention imparts no wrong influences to eyes and is naturally safe for eyes, and also does not any wrong influences to a soft contact lens when the lens is electrically treated. Also, since the electric conductivity of the treating solution of the present invention is smaller than the electric conductivity of conventionally used soaking solutions for a soft contact lens, the solution can be easily distinguished from these soaking solutions for a soft contact lens.

We claim:

1. A method for cleaning and disinfecting a soft contact lens which comprises:
   immersing a soft contact lens in a treating solution which is an aqueous solution of an electrolyte, the concentration of said electrolyte being 0.001 to 0.5 mol/l and said electrolyte being at least one member selected from the group consisting of a boric acid salt buffer, a phosphoric acid salt buffer, a citric acid salt buffer, an oxalic acid salt buffer, a succinic acid salt buffer, a tartaric acid salt buffer, $K_2CO_3$, $Na_2CO_3$, $NaHCO_3$, $Na_2SO_4$ and sodium acetate and having a pH of 6 to 7.5; and
   applying a direct current of 0.1 to 5 A to the treating solution to raise the temperature of the treating solution to at least 80° C. and to remove stains from the soft contact lens.

2. The method for cleaning and disinfecting a soft contact lens of claim 1, wherein the treating solution has an electric conductivity of at most 8 mS/cm.

3. The method for cleaning and disinfecting a soft contact lens of claim 1, wherein the applying period of time of an electric current is in the range of 10 to 30 minutes.

* * * * *

TABLE 3

| Ex. No. | Ingredients (w/v %) | | | pH | Osmotic pressure (mmol/kg) | Electric conductivity (mS/cm) |
|---|---|---|---|---|---|---|
| | Boric acid | Borax | Sodium citrate ($Na_3C_6H_5O$) | | | |
| 1 | 1.35 | 0.15 | 0 | 7.01 | 250 | 0.60 |
| 2 | 1.80 | 0.04 | 0 | 6.00 | 285 | 0.20 |
| 3 | 2.10 | 0.10 | 0 | 6.51 | 330 | 0.38 |
| 4 | 1.76 | 0.04 | 0 | 6.05 | 286 | 0.16 |
| 5 | 1.80 | 0.04 | 0.2 | 6.38 | 300 | 1.42 |
| 6 | 1.35 | 0.15 | 0.6 | 7.32 | 276 | 5.00 |
| 7 | 1.35 | 0.10 | 1.0 | 7.26 | 293 | 7.30 |
| 8 | 0.96 | 0.12 | 1.0 | 7.50 | 254 | 7.30 |